(12) United States Patent
Ebbesen et al.

(10) Patent No.: US 8,174,696 B2
(45) Date of Patent: May 8, 2012

(54) DEVICE FOR SORTING AND CONCENTRATING ELECTROMAGNETIC ENERGY AND APPARATUS COMPRISING AT LEAST ONE SUCH DEVICE

(75) Inventors: Thomas Ebbesen, Strasbourg (FR); Torbjorn Skauli, Oslo (NO)

(73) Assignees: Universite de Strasbourg, Strasbourg (FR); Centre National de la Recherche Scientifique, Paris (FR); Forsvarets Forskningsinstitutt, Kjeller (NO)

(*) Notice: Subject to any disclaimer, the term of this patent is extended or adjusted under 35 U.S.C. 154(b) by 245 days.

(21) Appl. No.: 12/532,499

(22) PCT Filed: Mar. 25, 2008

(86) PCT No.: PCT/IB2008/001285
§ 371 (c)(1),
(2), (4) Date: Dec. 16, 2009

(87) PCT Pub. No.: WO2008/114148
PCT Pub. Date: Sep. 25, 2008

(65) Prior Publication Data
US 2010/0110430 A1    May 6, 2010

Related U.S. Application Data

(60) Provisional application No. 60/907,136, filed on Mar. 22, 2007.

(51) Int. Cl.
*G01J 3/12* (2006.01)
(52) U.S. Cl. ........................................ 356/331
(58) Field of Classification Search .................. None
See application file for complete search history.

(56) References Cited

U.S. PATENT DOCUMENTS

| | | | |
|---|---|---|---|
| 2003/0103150 A1 | 6/2003 | Catrysse et al. | |
| 2004/0046128 A1 | 3/2004 | Abel et al. | |
| 2005/0110990 A1* | 5/2005 | Koo et al. | 356/301 |
| 2005/0161589 A1 | 7/2005 | Kim et al. | |
| 2008/0174509 A1* | 7/2008 | Williams | 343/872 |

FOREIGN PATENT DOCUMENTS

| WO | WO 03/019245 A2 | 3/2003 |
|---|---|---|
| WO | WO 03/042727 A1 | 5/2003 |

OTHER PUBLICATIONS

International Search Report, dated Dec. 19, 2008.
A. Krishnan et al., "Evanescently coupled resonance in surface plasmon enhanced transmission", Optics Communications, 2001, pp. 1-7, vol. 200, Elsevier Science B.V.
Tineke Thio et al., "Diffracted Evanescent Wave Model for Enhancement and Suppression of Optical Transmission of Subwavelength Hole Arrays", Quantum Electronics and Laser Science Conference (QELS), 2005, pp. 1088-1090.

* cited by examiner

Primary Examiner — Tu Nguyen
(74) Attorney, Agent, or Firm — Young & Thompson

(57) ABSTRACT

A device for sorting and concentrating electromagnetic energy impinging a surface of the device, the surface including at least one plasmonics-based surface structure or similar structure of periodic or quasi-periodic surface topography. The device is characterized in that the surface (V) is provided with at least two such surface structures (2), acting as individual concentrator structures, which are at least partially spatially overlapped or superposed.

22 Claims, 7 Drawing Sheets

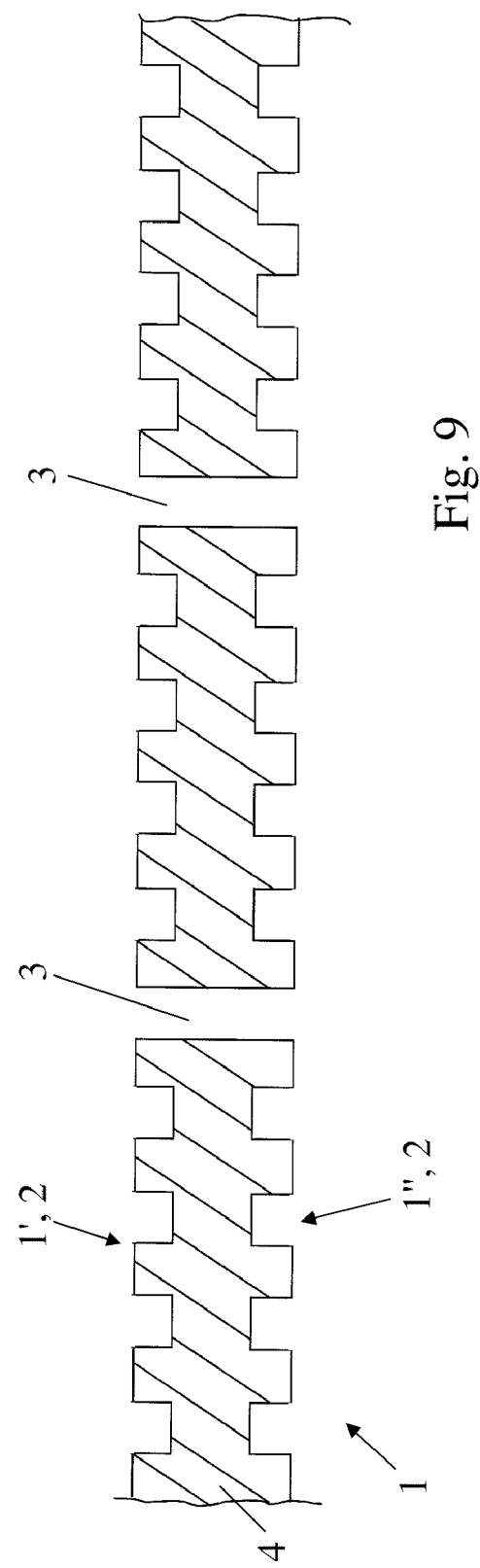

DEVICE FOR SORTING AND CONCENTRATING ELECTROMAGNETIC ENERGY AND APPARATUS COMPRISING AT LEAST ONE SUCH DEVICE

CROSS-REFERENCE TO RELATED APPLICATIONS

The instant application claims priority to PCT/IB2008/001285 filed Mar. 25, 2008 and Application 60/907,136 filed Mar. 22, 2007.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION (1) Field of the Invention

The present invention is related to the field of treatment of electromagnetic energy, in particular of optical energy, more specifically in the infrared and visible wavelengths, and concerns a device for sorting and concentrating electromagnetic energy of radiations with different properties, as well as an apparatus comprising at least one such device.

(2) Description of Related Art

Even though the present invention is more specifically described in relation to visible light or infrared radiations, it should be understood that a much wider range or types of electromagnetic radiations can be impacted by this invention, more specifically radiations ranging in matter of wavelength from microwaves to ultraviolet radiations.

In particular, in a wide variety of optical sensing applications, there is a need for devices able to characterize the spectrum (i.e. wavelength distribution) of incoming radiation (light). There are also applications which require characterization of the polarization state of the radiation or light. Almost invariably in these applications, there is a need to make efficient use of the available light while preserving signal integrity. This is normally combined with constraints on device size and/or cost.

Current imaging technology is based on arrays of light sensors, for example arrays based on silicon CCD or CMOS technology. In a basic imaging system using a two-dimensional matrix array of light sensors, the signal from each sensor element corresponds to one pixel in the image.

Spectral and polorometric imaging faces a general technological challenge in that the image data are essentially three-dimensional (with spectral or polarimetric information constituting a third dimension) while light sensor arrays generally are limited to two dimensions.

For color imaging, it is common to use a matrix array of light sensors equipped with individual color filters, each passing one of the primary colors, arranged in a so-called "Bayer pattern" or similar.

In this case, the partial images corresponding to each primary colour are not spatially registered, and some form of interpolation is needed to estimate, for each pixel, the amount of light in the two primary colours not passed by the spectral filter of the corresponding light sensor element. This can lead to color artefacts in the resulting image.

Also, each light sensor element collects only light within its own spectral band, and thereby the rest of the light impinging on that particular element is lost.

There is a general demand to overcome the limitations exposed herein before, for applications in connection with the handling, treatment and/or exploitation of visible light, as well as other electromagnetic radiations having longer or shorter wavelengths.

On the other hand, there has been, in recent years, significant progress in the understanding and exploitation of charge oscillation phenomena at optical frequencies on metal surfaces, a field known as plasmonics [see for example: Barnes et al., Nature vol. 424, p. 824, 2003; C. Genet and T. W. Ebbesen, Nature vol. 445 p. 39 (2007)].

Indeed, surface plasmons (SPs) have generated considerable interest recently due to their potential in optics and sensing, among numerous other applications [see for example: Zayats, A. V., Smolyaninov, I. I & Maradudin, A. A. "Nano-optics of surface plasmon polaritons." Phys. Rep. 408, 131-314 (2005) ; Mikhailov, V., Wurtz, G., Elliot, J., Bayvel, P., Zayats, A. V. "Dispersing Light with Surface Plasmon Polaritonic Crystals." Phys. Rev. Lett. 99, 083901 (2007); Zia, R., Schuller, J. A., Chandran, A., Brongersma, M. L. "Plasmonics: the next chip-scale technology." Materials Today. 9, 20-27 (2006)].

Surface plasmons are essentially light waves trapped at a metal surface by their interaction with the free electrons in the metal. Their properties can be controlled by texturing the metal surface. In the context of spectral and polarizing imaging, single apertures surrounded by periodic grooves are of particular interest [see for example: Thio, T., Pellerin, K. M., Linke, R. A., Lezec, H. J. & Ebbesen, T. W. "Enhanced light transmission through a single subwavelength aperture." Opt. Lett. 26, 1972-1974 (2001); Nahata, A., Linke, R. A., Ishi, T. & Ohashi, K. "Enhanced nonlinear optical conversion from a periodically nanostructured metal film." Opt. Lett. 28, 423-425 (2003); Garcia-Vidal, F. J., Lezec, H. J., Ebbesen, T. W. & Martin-Moreno, L. "Multiple paths to enhance optical transmission through a subwavelength slit." Phys. Rev. Lett. 90, 213901 (2003)].

The periodic grooves act like an antenna for the incoming light by converting it to surface plasmons and enhancing the transmission through the aperture.

FIG. 1 gives an example of one such aperture structure where a single subwavelength hole is surrounded by concentric grooves.

Such a structure, also known as "bull's eye" structure can, for example, be milled by focused ion beam (FIB) lithography in the surface of a metal film (for example made of silver or gold). Such a device may be for visible light for example a 300 nm thick Ag film on a glass substrate with a structure having the following dimensions: diameter of central hole: 170 nm; width of grooves: 150 nm; depths of grooves: between 10 nm and 150 nm; spatial period: 600 nm.

As indicated by the arrows, incident light excites surface charge oscillations, and the optical energy is concentrated at the center of the structure where it enters an aperture in the film. The light emerges at the back side of the film where, depending on the structuring of the back side, the light may diffract out as indicated. The structure preferentially collects light within a band of wavelengths determined mainly by the period of the ring structure. At the bottom is an image of an actual bull's eye structure fabricated in a gold film.

The transmission peak wavelength $\lambda_{SPP}$ of such a structure can be tuned by controlling the groove periodicity P (FIG. 1b) as predicted by equation (1) for normal incidence illumination:

$$\lambda_{SPP} = P\sqrt{\frac{\varepsilon_m \varepsilon_d}{\varepsilon_m + \varepsilon_d}} \quad (1)$$

where $\varepsilon_m$ and $\varepsilon_d$ are the dielectric constants of the metal and the dielectric in immediate contact with the metal surface. The peak is normally red-shifted compared to the prediction of equation (1) due to Fano-type interaction. The transmission spectrum is also modulated by the other structural parameters such as groove depth, width, aperture shape and size, as indicated in the previously quoted references.

Such a structure preferentially collects optical energy within a band of wavelengths adapted to its period.

The surface plasmons give rise to intense electromagnetic fields at the central hole. The flux per unit area through the aperture can be larger than that of the incident light, confirming that the grooves act as an antenna, collecting light laterally from an area around the hole. This extraordinary transmission phenomenon allows for useful light collection efficiencies even though the apertures represent only a small fraction of the surface of the device, the optical energy being extracted at the back of the film, at the exit opening of the aperture, after passing through the latter.

Another example of a known radiation or light concentrating structure consists of a metal film with linear corrugations surrounding a slit-shaped aperture in which the optical or radiative energy is concentrated, as illustrated in FIG. 2. The concentrating effect of this structure depends not only on the wavelength, but also on the polarization of the incoming light or radiation.

Now, the inventors have discovered unexpectedly that plasmonics based surface collector structures can be applied to realise at least a spectrally differentiated or polarisation selective collection, and therefore a characterisation of the spectral properties, of electromagnetic radiations, and in particular of light, which allows in particular to overcome the above mentioned limitations in respect of the known Bayer-mask technique.

BRIEF SUMMARY OF THE INVENTION

Thus, according to the invention there is proposed a device for sorting and collecting electromagnetic energy impinging a surface of said device, said surface comprising at least one plasmonics-based surface structure or a similar surface structure having one or more specific resonance(s), characterised in that said surface is provided with at least two such surface structures, acting as individual collector structures, which are at least partially spatially overlapped or superposed.

This inventive basic concept allows, depending on the design and layout of each of the intermeshed individual surface structures, to sort out and to concentrate radiation components having different specific properties, the overlapped areas acting surprisingly without noticeable mutual interference.

Advantageous embodiments or additional features of the device according to the invention are disclosed.

Such a device can in particular be used to perform spectroscopy or polarimetry.

The present invention also concerns an apparatus for separating and characterising an electromagnetic radiation impinging the surface(s) of at least one thin plate or film like body, characterised in that said body or each of said bodies consists of a device as described before, wherein each radiation component sorted by one of the concentrator structures is concentrated at an entry opening of a corresponding aperture and wherein a sensor or a group of sensors is arranged on the side of the body opposite the impinging surface to collect information of the separated radiation components emanating from the exit opening(s) of one or several apertures.

Such an apparatus can for example be used to perform spectral and/or polarimetric imaging, as well as colour imaging.

An application of that kind is for example described in: "Plasmonic photon sorters for spectral and polarimetric imaging", E. Laux et al., Nature Photonics, Vol. 2, 161-164 (2008).

The present invention further concerns an apparatus for combining electromagnetic radiations having different properties and delivered by different sources into a single electromagnetic radiation, characterised in that it comprises at least one device as described before, wherein the radiation emitted by each source is fed into a corresponding aperture of said body through its exit opening, said different radiations being combined as constitutive components into a single radiation emitted from the surface provided with the concentrator structures.

Such an apparatus can for example be used to perform image display or projection.

Other objects of the present invention are mentioned in the enclosed claims and will become more readily apparent in light of the following description in conjunction with the following accompanying drawings, wherein:

BRIEF DESCRIPTION OF THE SEVERAL VIEWS OF THE DRAWINGS

FIG. 9 is a schematical cross-sectional view of a device according to an other embodiment of the invention, similar to the one shown on FIG. 3 but also provided with concentrator structures on its exiting surface.

DETAILED DESCRIPTION OF THE INVENTION

Figure 1:
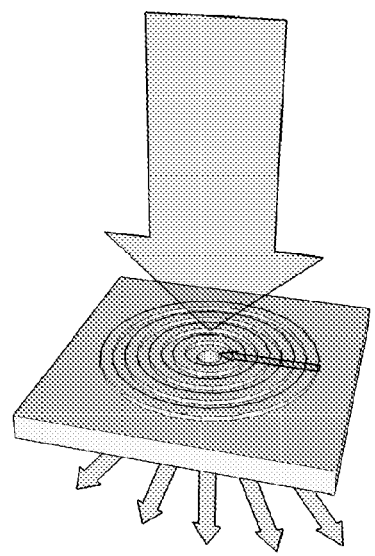
FIG. 1 gives an example of one such aperture structure where a single subwavelength hole is surrounded by concentric grooves.
Figure 2:
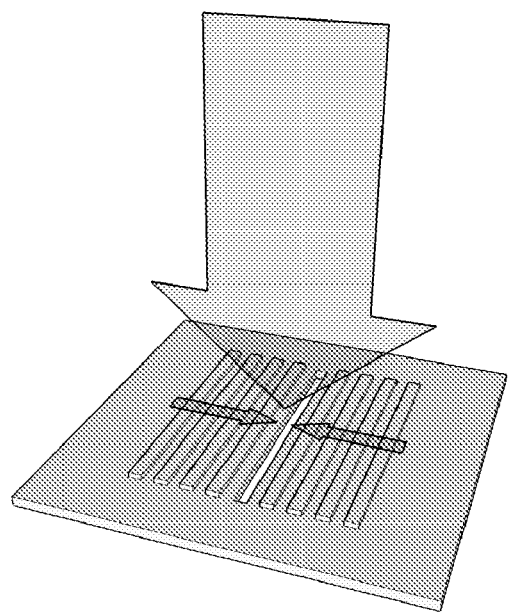
FIG. 2 illustrates a known radiation or light concentrating structure consists of a metal film with linear corrugations surrounding a slit-shaped aperture in which the optical or radiative energy is concentrated.

Central to this invention is the use of overlapping, or superposed, plasmonic collector structures, such as those in FIGS. 1 and 2, to collect and to concentrate different wavelengths or polarizations at separate locations.

Indeed, a key characteristic of the invention is that electromagnetic radiation, for example light, containing different spectral and/or polarization components impinging on the overlapping area can be separated laterally by the inventive device, according to the properties of the different components. The energy in the different components is preferentially concentrated in different locations. Such decomposition is a basic building block enabling, among others, spectroscopic and polarimetric sensing.

Figure 8:
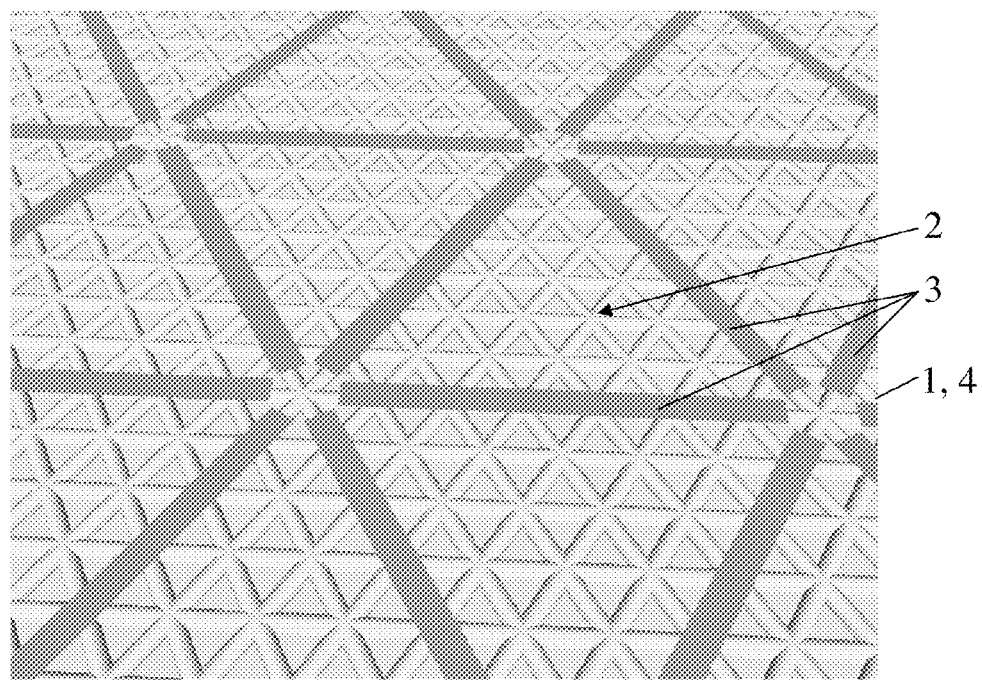
FIG. 8 is a partial perspective top view of a device according to an other embodiment of the invention, adapted for polarimetric imaging. An array of slits is fabricated in a metal film with corresponding corrugations. The slits will receive optical energy from the neighbouring set of parallel corrugations with a strength dependent on the polarization of the incident light. Individual light sensor elements (not shown) placed under each of the slits record signals which may be used to construct a polarimetric image.

The surface overlapping rate can be from several tens of percent (for example: 30%, 50%, 70%) up to 100% (cf. FIG. 8).

Figure 3A:
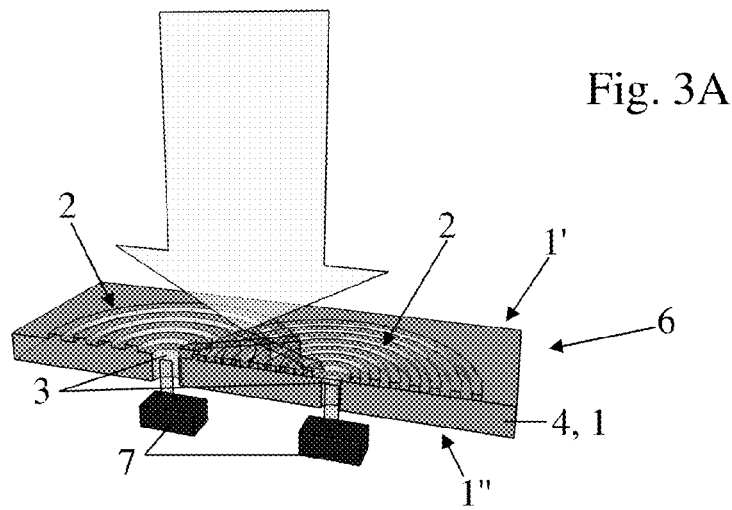
FIG. 3A is a cross-sectional perspective view of an apparatus for separating and characterising an electromagnetic radiation, in particular light, which incorporates a device according to a first embodiment of the invention. This embodiment of the device consists of two overlapping bull's eye concentrator structures, concentrating different spectral components of the incoming light. Two light sensor elements are placed underneath the metal film according to the invention, receiving the optical energy concentrated by each of the bull's eyes structure. Such an assembly may be used to collect signals containing information about the spectral distribution of incoming light.
Figure 3B:
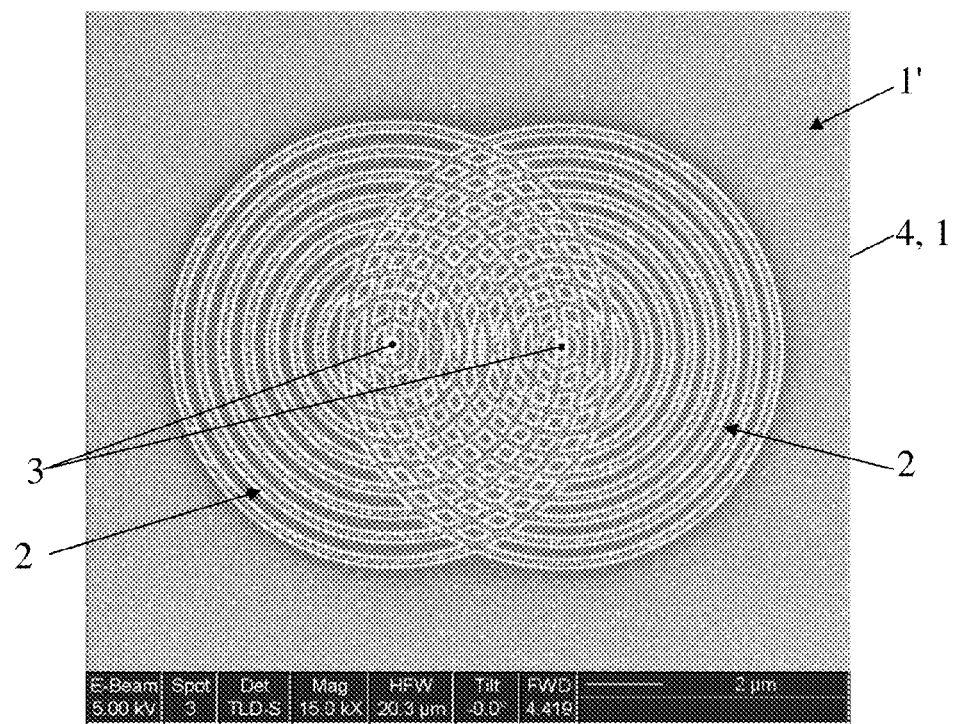
FIG. 3B is a top view of an embodiment similar to FIG. 3A made of a pair of overlapping bull's eye structures fabricated in the surface of a gold film according to the invention.

This is exemplified by the pair of overlapping bull's eye structures with different periods milled in a gold film, shown in FIG. 3. Here light impinging on one of the structures, with a wavelength matching the period of that structure, will be preferentially concentrated at the center of that structure. This is the case even for light incident on the overlap area. Thus, each structure will collect a different spectral component of the light incident on the overlap area. Depending on the center to center distance and the layout of the light concentrating structures fabricated according to the invention, the overlap area may extend over most, or all, of the area occupied by the combined structure.

According to the invention, a light sensor may be placed under each aperture to collect information on the spectral content of light incident on the combined light concentrator structures, as indicated in FIG. 3A. Even if the light sensors are laterally separated, the overlapping light collection structures enable both light sensors to efficiently collect light from most, or all, of the area occupied by the combined structure.

According to the invention, the basic principle just described can be extended to more spectral components, or polarization components, by increasing the number of overlapping concentrator structures.

Figure 4A:
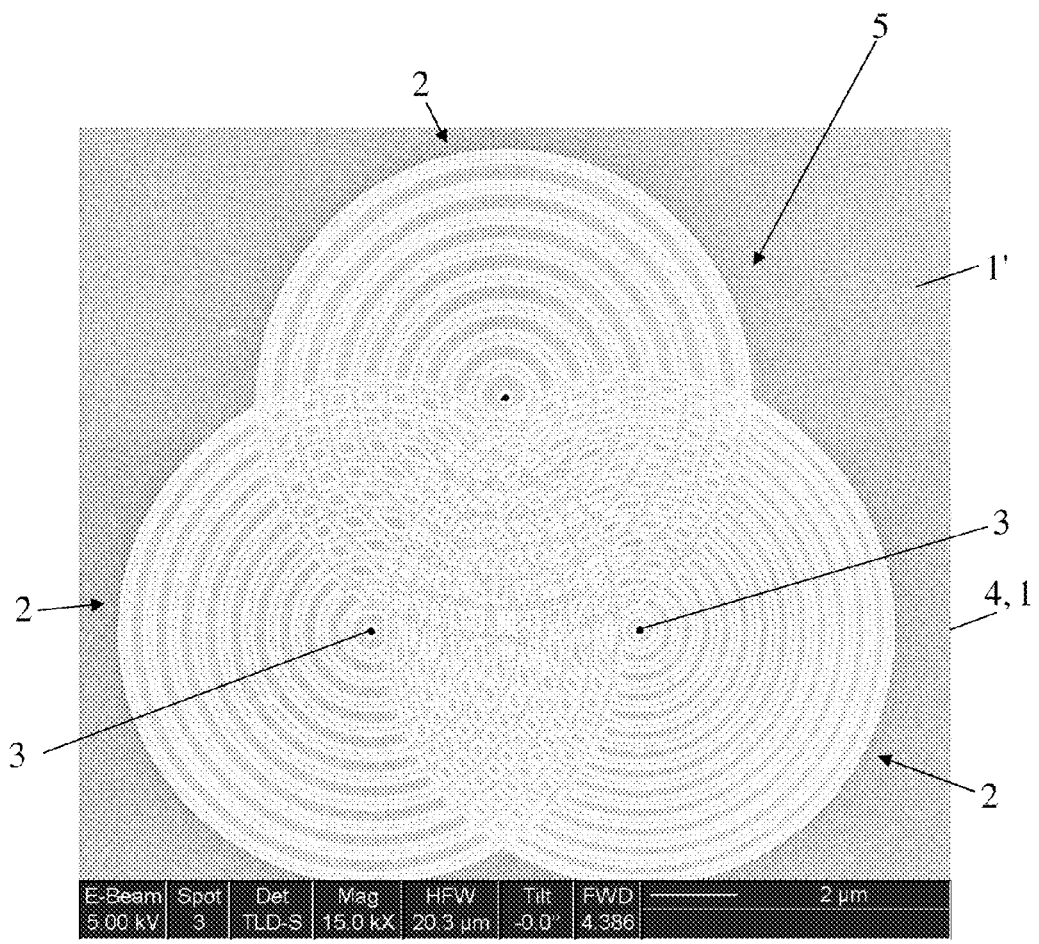
FIG. 4A is a top view of a device according to a second embodiment of the invention. This embodiment consists of three partially overlapping bull's eye concentrator structures fabricated in the surface of a gold film. Each concentrator structure has a different periodicity of the rings. Thus, the structures preferentially concentrate three different spectral components of the incident light.
Figure 4B:
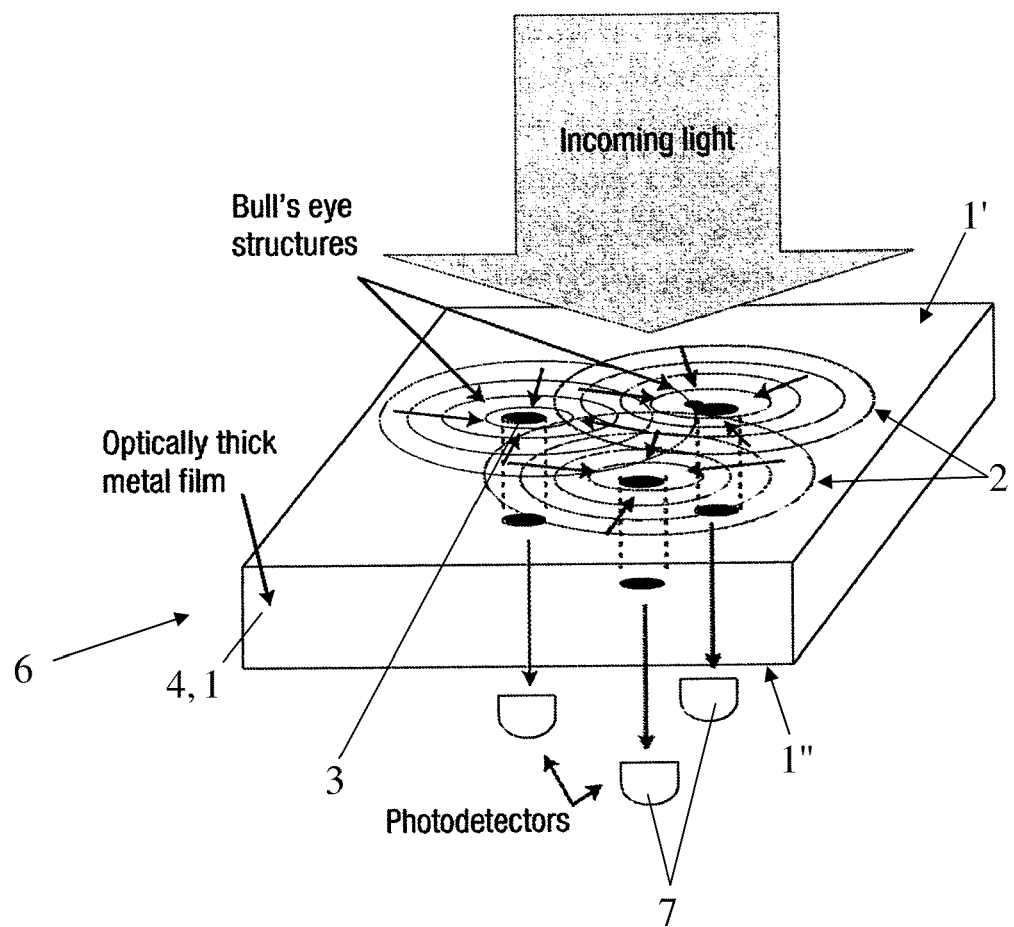
FIG. 4B is a shematical perspective view of an apparatus for separating and characterising an electromagnetic radiation (light) incorporating a device as shown on FIG. 4A.

This is illustrated in FIG. 4A for a triple light collecting device. Here the three bull's eye structures have different periods in order to collect three different spectral components of the incident light. An analogous scheme for characterizing polarization will be described below.

Figure 5:
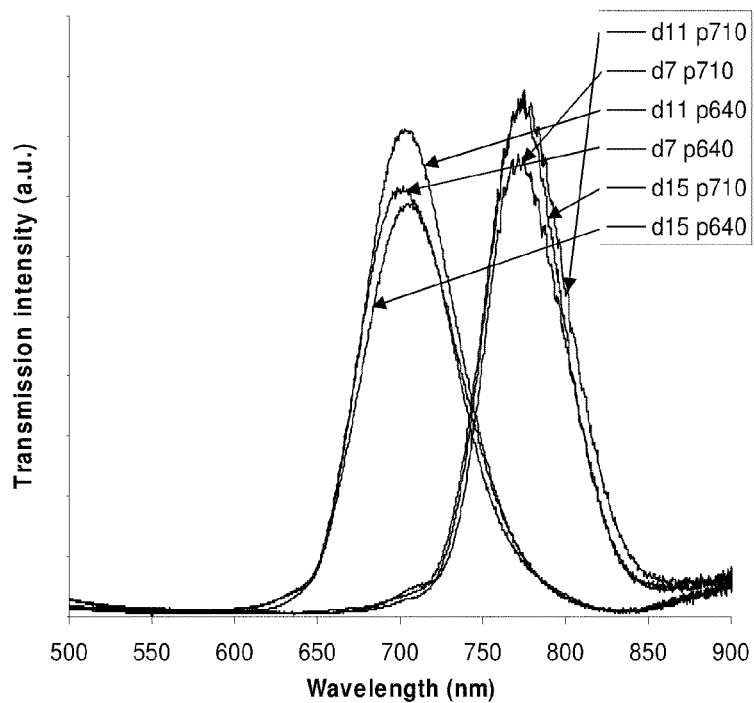
FIG. 5 is a graph showing the measured total transmission spectra of three different double concentrator structures similar to the one shown in FIG. 3, each with different separation of the two central holes. The structures are fabricated in a 300 nm thick silver film. Each bull's eye structure has a radius of about 7 micrometers. The figure shows measurements for center-to-center spacings of 7, 11 and 15 micrometers. It can be clearly seen that the position of the main transmission peaks remains essentially unaffected by the degree of overlap between the two concentrators which is about 30% in the case of 7 micrometer spacing.

The results shown in FIG. 5 demonstrate how such overlapping structures can separate components of the light incident on the overlap area and bring the optical energy to the respective apertures at the center of each structure. In the figure, the light transmitted by the apertures of two bull's eye structures with different periods is compared when they are far apart and when the center-to-center distances are 7 um. The latter case corresponds to an overlap of about 30%. When the light collector structures are far apart, they have a transmission peak defined mainly by their period. In the overlapped structure, each aperture still has a distinct spectrum dominated by the spectral characteristics of the isolated bull's eye structure.

Figure 6:
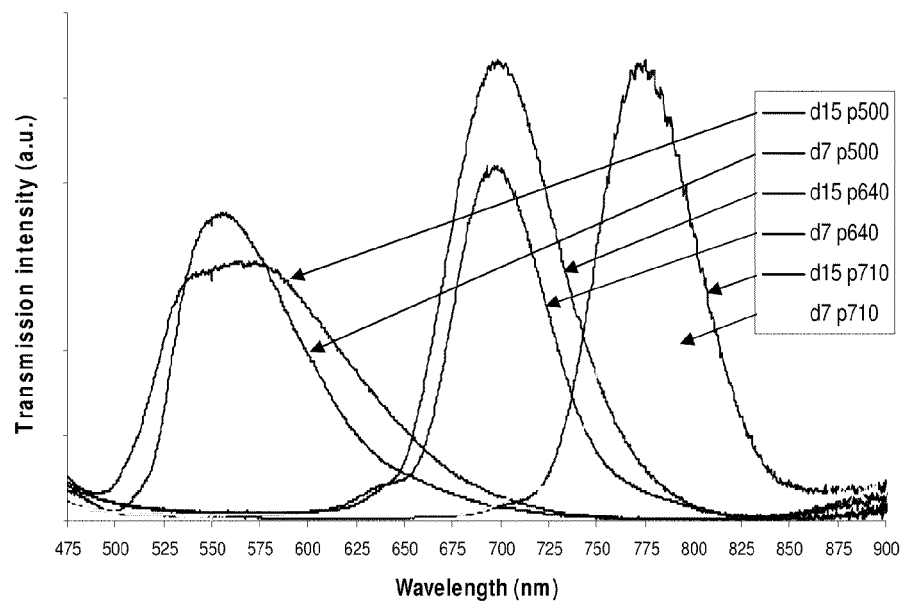
FIG. 6 is a graph showing the measured strength of each transmission peak for a combination of three concentrator structures with different periodicities fabricated in a 300 nm thick silver film when they have an overlap of 50% (d7) and when the spacing is larger so that there is no overlap (d15). The overlap is defined here as the fraction of the area of one bull's eye overlapping with one or more of the neighbouring structures. The strength of the transmission peaks decreases much less than the amount of overlap. This shows that even for light incident on the overlap area, optical energy is being preferentially concentrated at different apertures depending on wavelength.

If the transmission at the three preferential wavelengths defined by the three periods is plotted as a function of overlap between the three structures, one notices that the overlap introduces very little loss relative to the isolated structures as shown in FIG. 6. This result further confirms the ability of the overlapping concentrators to laterally separate light impinging on the overlap area, in this case a separation according to wavelength. This provides a clear proof of concept of the invention.

An assembly of light concentrator structures and light sensors according to the invention can be used to characterize the spectral and/or polarimetric properties of light impinging on a localized area defined by the light concentrator structures. Such an assembly in itself can have important applications such as highly compact spectrometers.

By analyzing light impinging on a localized area, the said assembly performs the functions needed to collect the signals corresponding to one pixel of a spectral and/or polarimetric image. It will therefore be referred to such an assembly as a "superpixel" hereinafter.

Figure 7:
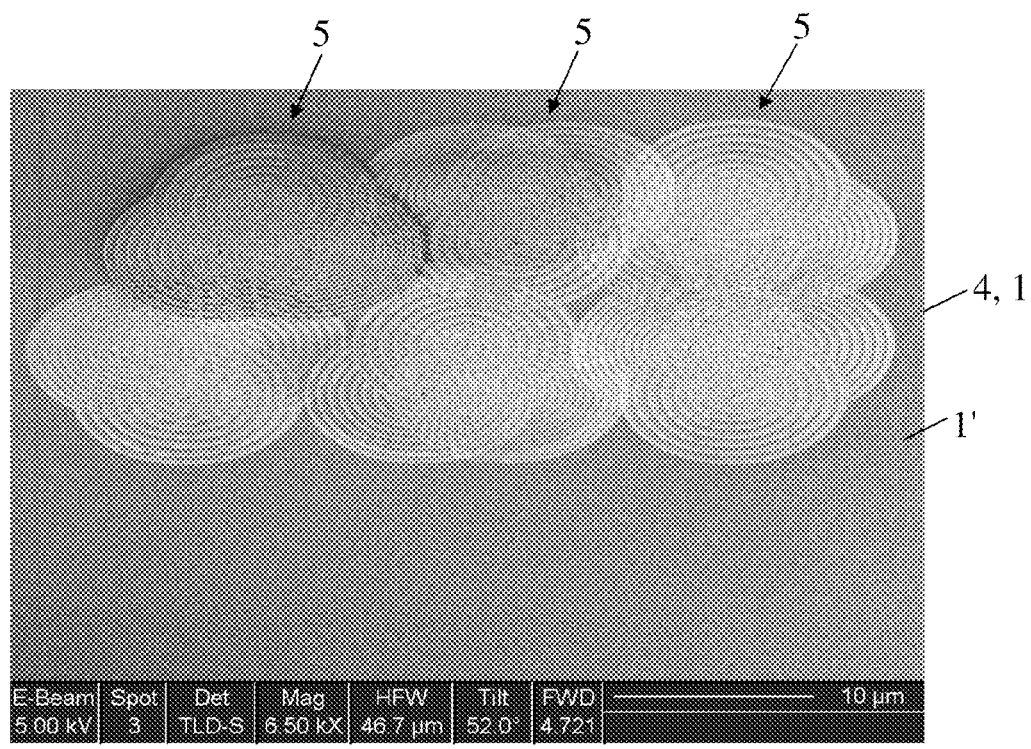
FIG. 7 is a perspective top view of a device according to an other embodiment of the invention, comprising an array of partially overlapped groups of concentrator structures fabricated in a gold film, each with three bull's eye structures of different wavelength. Overlapping concentrator arrays such as this may be used to perform spectral or polarimetric imaging.

According to the invention, it is possible to fabricate an array of multiple superpixel units, for example by arranging the light concentrator structures as shown in FIG. 7.

By placing such an array of superpixels at the focus of suitable imaging optics, the collected output of the light sensors in all superpixels will constitute a spectral and/or polarimetric image. The resulting spectral imaging system will exhibit better spectral registration between bands and has potential to make more efficient use of the light, compared to an imaging system based on Bayer mask filters or similar.

An important aspect of the invention is that the optical energy is concentrated in a small area, potentially smaller than the free-space wavelength of light, even if the light sensitive area of the superpixel unit is significantly larger.

This enables the use of very small light sensor elements, typically fabricated as a monolithic array on a semiconductor chip.

Use of small light sensor elements according to the invention is advantageous in several ways including the following:

Firstly, this enables the use of more closely spaced light sensor elements compared to "Bayer mask" or similar technologies, with a resulting potential to reduce the total area required for the light sensor array.

Secondly, the size of the light sensor elements is an important factor determining their speed of response (see for instance T. Ishi et al., Jpn. J. Appl. Phys. vol. 44 p. L364 (2005)).

Thirdly, the size of the light sensor element may also determine the strength of important contributions to sensor noise, depending on the sensor technology.

A fourth advantage is that the use of plasmonic light concentrators avoids the need for a light sensor array with a high ratio of light sensitive area to total area, known as "fill factor". A reduced requirement on fill factor may provide opportunity to increase the functionality of the chip carrying the light sensor array, or it may be translated into cost savings on the light sensor array fabrication.

Hereinafter, it will be outlined in more detail how the invention may be used to characterize the polarization state of light, including polarimetric imaging.

One way to derive polarimetric information is to use overlapping structures of the type shown in FIG. 2, oriented in different directions.

For instance, the structure shown in FIG. 8 combines different polarization dependent light collecting structures that overlap in a triangular lattice.

In this complex structure, each edge of a given triangle is a slit aperture collecting light from the neighbouring set of corrugations parallel to the slit. By placing photodetectors below each slit, it is possible to record polarimetric information of the incident light and, in conjunction with suitable imaging optics, to form a polarimetric image.

The light transmitted by the apertures described above normally diffracts as it emerges on the opposite side of the film. It is known (see for example Lezec et al., Science vol 297, p. 820, 2002, Martin-Moreno et al., Phys. Rev. Lett. vol. 90, 167401, 2003 and U.S. Pat. No. 7,057,151) that the diffraction at the exit of the aperture can be controlled by structuring the surrounding output surface of said aperture.

By the appropriate choice of structuring, the emerging light can be focused and beamed either normal to the surface or with an oblique angle. According to the invention, the structuring on the output side may consist of combined or overlapping structures for focusing or beaming different components of light in different directions. In this manner it is possible to further separate the light on the output side, for example by directing different polarizations onto different light sensor elements.

An important general aspect of the invention is the use of spatially overlapping, or superposed, plasmonic structures capable of separately concentrating the optical energy of components of light with different characteristics such as wavelength, polarization, angle of incidence or combinations thereof. According to the invention, any number of plasmonic concentrator structures may be combined in this way, and the overlap may be partial or complete. The overlapping may be accomplished in many ways depending on performance requirements and fabrication capabilities.

According to the invention, one way to use the said overlapping light-concentrating structures is to couple light sensors to each of the overlapping concentrator structures in order to measure the strength of the separated components of light.

According to the invention, it is also possible to use the overlapping concentrator structures in reverse to combine light from different sources, with the output light having properties such that it appears to come from a single source. Thus, another aspect of the invention is that it is possible to use the overlapping plasmonic structures to generate, or display, an image by replacing light sensors with light sources. This could find use in image projectors or displays.

Many alternative embodiments of the invention will be apparent to those skilled in the art. For instance, the periodic structures can be made of grooves or protruding structures on the metal film. The periodic structures can be made of metal or dielectric material. The preferred metal depends on the properties of the metal at the wavelength of interest. In the visible range, silver is the preferred metal while in the infrared gold is also very good. The central aperture may have a variety of shapes and may be smaller or larger than the wavelength. The boundaries between superpixels may be delineated in various ways to define the sensitive area of the superpixel. This may include truncating individual concentrator structures at boundary lines between superpixels, as well as means to control the propagation of charge oscillations across the superpixel boundaries.

An important class of relevant applications of the invention is spectral imaging. (Here the term "spectral imaging" is used to refer to imaging techniques which resolve incoming light not only spatially, but also spectrally. This includes "multispectral imaging", which normally refers to systems with 2 to 10 different spectral channels, as well as "hyperspectral imaging" which normally refers to systems with tens or hundreds of spectral channels.) A typical spectral imaging system forms an image consisting of individual pixels, and for each pixel information is recorded about the wavelength distribution of the incoming light. The most common form of spectral imaging is color imaging, which images visible light separated into three spectral channels corresponding to the primary colours of the human eye. It is well known that this colour information strongly increases the information content of the image compared to the case of monochrome imaging ("black and white", no spectral information). Furthermore, it is a well established fact that the addition of more spectral channels, such as in hyperspectral imaging, adds significant extra information which greatly facilitates automated computer analysis of the images.

In addition to its spectral distribution, an incoming light signal is also characterized by its polarization state, which often carries valuable information. In analogy with spectral imaging, polarimetric imaging refers to techniques that form images in a way which is sensitive to polarization state. It is known that applications ranging from surface inspection to military target detection may benefit from measurement of polarization state, for example through polarimetric imaging.

In the foregoing specification, illustrated by the enclosed drawings, the invention has been mainly described in view of applications related to visible light.

However, according to the invention, the same dispositions and features, including polarization-dependent structures, can be extended to other wavelengths such as thermal and microwave regions essentially by scaling the structures and choosing appropriate light sensors (or sources). One possible application is spectral or polarimetric imaging at thermal infrared wavelengths, which can be of interest in military applications. At longer wavelengths, fabrication is facilitated by the larger dimensions of the concentrator structures. In general, many other applications will be apparent to those skilled in the respective application areas. For example, a single "superpixel" as discussed above may be used as a highly compact spectrometer device suitable, among other things, for coupling to an optical fiber or inclusion in microsystems.

The following non limitative numerical references appear in the appending drawings and claims:
1: device
1': impringed surface
1": exited surface
2: individual surface structure
3: aperture/localised region of energy concentration
4: plate or film-like body
5: group of overlapping surface structures
6: apparatus
7: sensors While there has been described and illustrated various embodiments of the invention, it will be apparent to those skilled in the art that variations and modifications are possible without deviating from the spirit and broad teachings of the invention which shall be limited solely by the scope of the claims appended hereto.

The invention claimed is:

1. A device for sorting and collecting electromagnetic energy impinging a surface of said device, said surface being provided with at least two plasmonics-based or surface plasmons supporting surface structures having specific resonances and at least partially spatially overlapped areas,
wherein surface structures act as individual collector and concentrator structures and different at least one of spectral and polarisation components of electromagnetic radiation impinging on the overlapping areas are separated laterally according to properties of said components,
wherein each collector and concentrator structure is arranged so as to collect the electromagnetic energy the collector and concentrator structure is sorting out from the surface impinging energy, and to concentrate the electromagnetic energy at a corresponding specific region (3) situated within or outside said collector and concentrator structure, whereby electromagnetic energy of radiation components with different properties is concentrated at different localised regions, and
wherein each localised region (3) of energy concentration corresponds to an aperture in the impinged surface (1'), the impinged surface (1') corresponding to the surface of a thin plate or film-like body (4).

2. The device according to claim 1, wherein each surface structure forms a periodic or quasi-periodic surface topography.

3. The device according to claim 1, wherein each one among at least two different collector and concentrator structures which are partially or totally overlapped has at least one of specific dimensional and structural features adapted to concentrate electromagnetic energy having corresponding specific properties, in particular specific wavelength, at least one of angle of incidence and polarisation.

4. The device according to claim 1, wherein the least two collector and concentrator structures which are partially or totally overlapped have different spatial periods, at least one of structurings and arrangements, adapted to sort, collect and concentrate separately electromagnetic energy having either respectively corresponding different wavelengths or wavelengths within corresponding different wavelength ranges, at least one of respectively corresponding different polarisation directions and respectively corresponding different angles of incidence.

5. The device according to claim 1, wherein the said at least two collector and concentrator structures which are partially or totally overlapped are scaled to sort, collect and concentrate electromagnetic energy having wavelengths comprised within a range of values between 500 Angströms and 1 m.

6. The device according to claim 1, wherein each localised region (3) of energy concentration consists of a circular aperture in the impinged surface, the associated collector and concentrator structure being arranged in a concentric circular pattern around said aperture and the body (4) being possibly mounted on a support body made of a material which does not interact with a concerned radiation type.

7. The device according to claim 1, wherein each localised region (3) consists of an elongated slot-like or slit-like aperture in the impinged surface, the associated collector and concentrator structure being arranged in a linear pattern parallel to said aperture, on one or both side(s) of said aperture on said impinged surface, in a symmetric arrangement and the body (4) being mounted on a support body made of a material which does not interact with a concerned radiation type.

8. The device according to claim 1, wherein the at least two slots or slit-like apertures (3), of linear or non linear shape, are mutually arranged in a parallel or a non parallel disposition, the collector and concentrator structures associated with said apertures having at least one of identical spatial periods and shapes or not.

9. The device according to claim 1, wherein said thin plate or film-like body (4) is also provided with plasmonics-based collector and concentrator structures or similar structures of periodic or quasi-periodic surface topography on a surface (1") opposite the impinged surface (1'), said structures being each arranged around an exit opening of an aperture (3) of said body (4).

10. The device according to claim 9, wherein the collector and concentrator structures around the exit openings of the apertures (3) are dimensioned, structured and arranged in order to at least one of focus and direct in a given direction the respectively corresponding emerging electromagnetic radiation component, said exit collector and concentrator structures being possibly also partially or fully overlapped.

11. The device according to claim 1, wherein at least one of said impinged and exit surface(s) (1', 1") comprise(s) several groups (5) of at least two partially overlapped collector and concentrator structures, covering at least partially said surface(s).

12. The device according to claim 11, wherein the collector and concentrator structures belonging to neighbouring groups (5) partially overlap themselves.

13. The device according to claim 11, wherein collector and concentrator structures belonging to neighbouring groups are delineated by gaps, projections or similar surface structuring features provided in or on said plate or film-like body, able to restrict a flow of electromagnetic energy from one group to another and possibly truncating one or more of the collector and concentrator structures within the groups.

14. The device according to claim 1, wherein the impinged surface is provided with at least one group (5) of three partially overlapped collector and concentrator structures featured to sort, collect and concentrate at associated corresponding regions an optical energy of light with different properties, in particular at least one of different wavelengths and polarisations.

15. The device according to claim 14, wherein the impinged surface is provided with several adjacent groups of three partially overlapped collector and concentrator structures, the localised energy concentration regions in a form of circular or slot-like apertures being mutually arranged in a discontinuous or continuous triangular pattern, possibly forming an homogeneous pattern over at least a part of the surface.

16. The device according to claim 1, consisting of a thin plate or film-like body (4) provided with at least two partially overlapped collector and concentrator structures on its an impinged face (1'), which concentrate electromagnetic energy of radiations with different properties at entry openings of corresponding different apertures (3), wherein the opposite face (1") comprising exit openings of said apertures are also provided with collector and concentrator structures arranged around said exit openings, which focus and direct the radiations exiting said openings, said collector and concentrator structures being overlapped.

17. The device according to claim 16, wherein the collector and concentrator structures on the impinged and exited surfaces (1' and 1") are arranged in groups of at least two different collector and concentrator structures, covering at least partially each surface.

18. The device according to claim 16, wherein the film like body is made of metal, the features forming the collector and concentrator structures consisting of grooves engraved or milled into said body or of protruding structures formed or deposited on the corresponding surface and made of metal or dielectric material.

19. The device according to claim 1, wherein the impinged surface (1') is a plane surface.

20. The device according to claim 1, wherein the impinged surface (1') is a curved surface being one of spherical or parabolic in shape.

21. An apparatus for separating and characterising an electromagnetic radiation impinging the surface(s) of at least one thin plate or film like body, wherein said body or each of said bodies (4) consists of a device (1) according to claim 1,
wherein each radiation component sorted by one of the collector and concentrator structures is concentrated at an entry opening of a corresponding aperture (3) and wherein a sensor or a group of sensors (7) is arranged on a side of the body opposite the impinging surface (1') to collect information of separated radiation components emanating from an exit opening(s) of one or several apertures (3).

22. An apparatus for combining electromagnetic radiations having different properties and delivered by different sources into a single electromagnetic radiation, comprising at least one device according to claim 1, wherein the radiation emitted by each source is fed into a corresponding aperture of said body through an exit opening, said different radiations being combined as constitutive components into a single radiation emitted from the surface provided with the collector and concentrator structures.

\* \* \* \* \*